United States Patent [19]

Katsuragi et al.

[11] Patent Number: 4,995,393

[45] Date of Patent: Feb. 26, 1991

[54] ALIGNMENT APPARATUS OF NONCONTACT TYPE TONOMETER

[75] Inventors: Kenjiro Katsuragi; Kouji Nishio, both of Tokyo, Japan

[73] Assignee: Kabushiki Kaisha Topcon, Japan

[21] Appl. No.: 333,949

[22] Filed: Apr. 6, 1989

[30] Foreign Application Priority Data

Apr. 8, 1988 [JP] Japan .................................. 63-86588

[51] Int. Cl.$^5$ .............................................. A61B 3/16
[52] U.S. Cl. .................................... 128/648; 128/652; 351/208
[58] Field of Search ............... 128/645, 648, 652, 748; 351/208

[56] References Cited

U.S. PATENT DOCUMENTS 3,756,073  9/1973  Lavallee ................................ 128/648
4,607,922  8/1986  Humphrey ......................... 351/208
4,817,620  4/1989  Katsuragi et al. .................. 128/648

Primary Examiner—Randall L. Green
Assistant Examiner—Randy Shay
Attorney, Agent, or Firm—Finnegan, Henderson, Farabow, Garrett & Dunner

[57] ABSTRACT

An alignment apparatus of a noncontact type tonometer has a target projecting system for projecting light emitted from a light emitting source to an eye to be tested along the axial line of a fluid discharging nozzle for discharging fluid and forming a target image on the eye, and an alignment light receiving optical system for receiving the target image along the axial line of the nozzle and forming an image of the target image on a light receiving sensor. The alignment apparatus of a noncontact type tonometer is characterized in that the light emitting source comprises a first and a second light emitting sources, the light receiving sensor comprises an area sensor, and the apparatus further has a control unit adapted to detect the positions of the target images of the first and second light emitting sources formed on the area sensor and to output an alignment completion signal when such detected positions are within a preset range on the area sensor.

7 Claims, 3 Drawing Sheets

FIG. 3
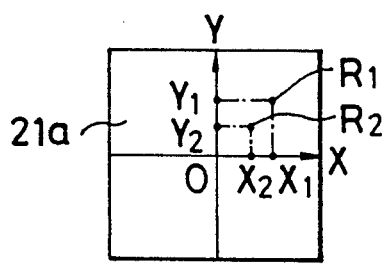
FIG.4(a)    FIG.4(b)    FIG.4(c)
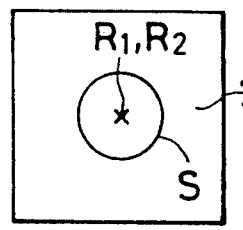 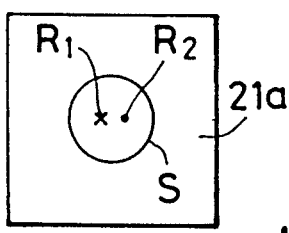 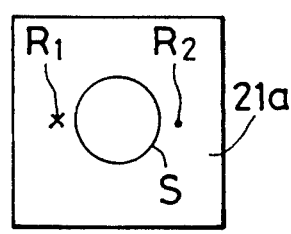
FIG.4(d)    FIG.4(e)    FIG.4(f)
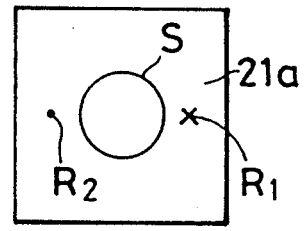 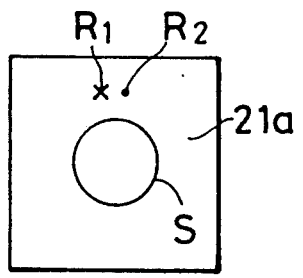 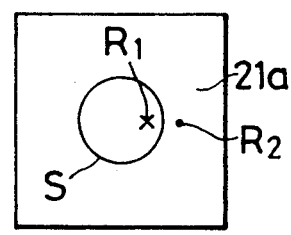

ALIGNMENT APPARATUS OF NONCONTACT TYPE TONOMETER

BACKGROUND OF THE INVENTION

1. Field of the Invention

This invention relates to an alignment apparatus of a noncontact type tonometer including a target projecting system for projecting light emitted from a light emitting source to an eye to be tested along the axial line of a fluid discharging nozzle adapted to discharge fluid and forming a target image on the eye, and an alignment light receiving optical system for receiving the target image along the axial line of the nozzle and forming the target image on a light receiving sensor.

2. Prior Art of the Invention

Heretofore, an alignment apparatus of a noncontact type tonometer includes a target projecting system for projecting a target image toward the center of curvature of the cornea of an eye to be tested along the axial line of a nozzle for discharging fluid such as air, etc., and a light receiving optical system for receiving a reflecting light reflected by the target image on the cornea along the axial line of the nozzle with a light receiving sensor thereof. And, the light receiving sensor is located in position where a light receiving quantity of more than a predetermined value of a reflecting light reflected by the target image when the alignment axial line of the eye and the axial line of an air pulse discharging nozzle are in alignment with each other and the distance between the eye and the nozzle is a predetermined distance. And, the alignment apparatus outputs an alignment completion signal when the light receiving quantity of the light receiving sensor reaches a predetermined value or more.

However, the conventional alignment apparatus of a non-contact type tonometer had such a problem as that since the alignment is determined by the received light quantity, the light receiving quantity of the light receiving sensor becomes a predetermined value or more and an alignment completion signal is issued when the alignment has not been completed, particularly in such events as that the cornea is suffered from a disturbance light or the eye to be tested is high in reflectance. Also, in the event that the cornea is low in reflectance, since the received light quantity does not become a predetermined value or more when the alignment has been completed, an alignment completion signal is not issued and it does not go to the eye pressure measuring step.

SUMMARY OF THE INVENTION

A first object of the present invention is to provide an alignment apparatus of a noncontact type tonometer, in which alignment can be detected without fail irrespective of the reflectance of an eye to be tested, disturbance light, etc.

A second object of the present invention is to provide an alignment apparatus of a noncontact type tonometer, in which alignment can be performed automatically.

The feature of the present invention is in that the light emitting source comprises a first and a second light emitting sources, the light receiving sensor comprises an area sensor, and there is included a control unit adapted to detect the positions of the target images of the first and the second light emitting sources formed on the area sensor and to output an alignment completion signal when the detected positions are within a preset range on the area sensor.

Another feature of the present invention is in that the light emitting source comprises a first and a second light emitting sources, and the light receiving sensor comprises an area sensor, the alignment apparatus further including a calculating circuit for calculating the positions of target images of the first and the second light emitting sources formed on the area sensor according to a signal output from the area sensor, a memory for storing therein the positions calculated by the calculating circuit, a control unit for outputting an alignment completion signal when the positions stored in the memory are within the preset range on the area sensor and outputting a control signal for moving an apparatus body in the alignment completing direction when the positions are outside the preset range, and a moving apparatus for moving the apparatus body in the alignment completing direction according to the control signal.

BRIEF DESCRIPTION OF THE DRAWINGS

FIG. 3 is a schematic view of an imaging point formed on a light receiving surface of a position sensor; and FIG. 4(a) through FIG. 4(f) are schematic views showing the relation between the setting range on the light receiving surface and the imaging point.

DETAILED DESCRIPTION OF THE EMBODIMENTS

One embodiment of the present invention will be described hereunder with reference to the accompanying drawings.

Figure 1:
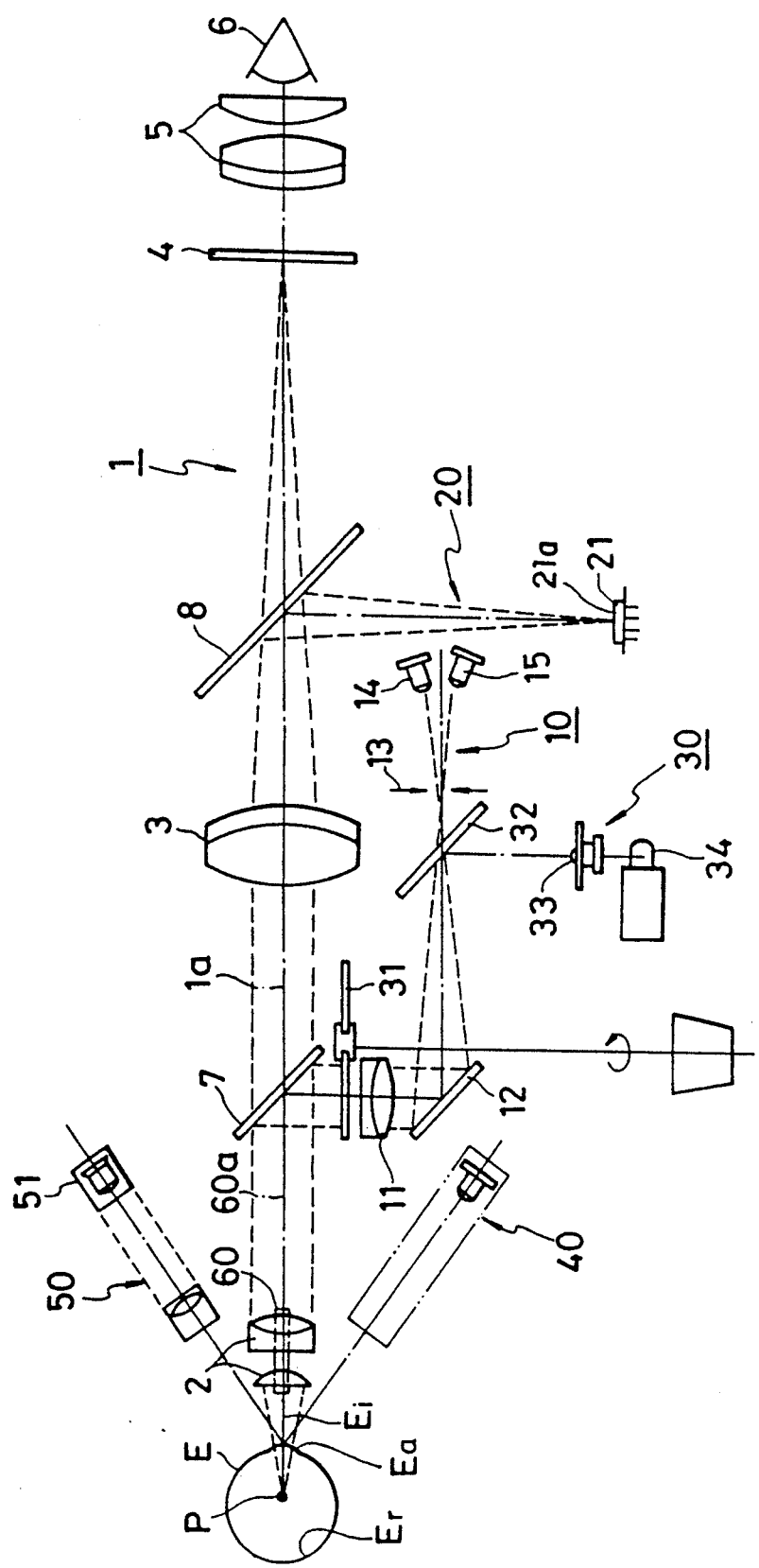
FIG. 1 is a conceptual view showing the arrangement of an optical system of a noncontact type tonometer according to the present invention.

FIG. 1 shows an arrangement of an optical system of a noncontact type tonometer according to the present invention. In FIG. 1, 1 denotes an observing optical system for observing an anterior portion of an eye E to be tested, 10 denotes a target projecting system for projecting a target image to the eye E in order to detect the state of alignment, 20 denotes an alignment light receiving optical system for receiving a reflecting light of a target image formed on the eye E, 30 denotes a fixation mark projecting system for projecting a fixation mark on the eye E, 40 denotes a detecting light projecting system for projecting a detecting light to a cornea Ea in order to detect the applanation state of the cornea 4a, and 50 denotes an applanation detecting light receiving system for receiving a detecting light reflected by the cornea Ea. The applanation detecting light receiving system 50 comprises a telecentric (an optical system including a diaphragm disposed in a focal point of an objective lens) light receiving device 51. 60 denotes a nozzle for discharging fluid such as, for example, air, etc. The nozzle 60 is disposed on the optical axis 1a of the observing optical system 1 which is a central portion of the objective lens 2.

And, the optical systems 1, 20, 50, the projecting systems 10, 30, 40 and the nozzle 60 are disposed on an apparatus body not shown. This apparatus body is moved in the directions of X-, Y- and Z-axes by a drive device 77 as will be described.

The observing optical system 1 comprises an objective lens 2 for collimating light from a virtual image P of the eye E as will be described, a lens 3 for forming an image of the virtual image P on an aiming circle 4, and an ocular 5 for observing an image formed in the aiming circle 4. 6 denotes an observing eye. The target projecting system 10 and the alignment light receiving optical system 20 constitute the optical system of the alignment apparatus.

The target projecting system 10 comprises an objective lens 2, a half mirror 7, a collimator lens 11, a mirror 12, and two light emitting diodes 14, 15 (the first and the second light emitting sources) as targets. Arrows 13 indicate the location of a diaphragm. The target images by the light emitting diodes 14, 15 are formed on the eye E as virtual images P. Also, the light emitting diodes 14, 15 are alternately blinked by a control circuit 76 as will be described.

The light receiving optical system 20 comprises an objective lens 2, a lens 3, a half mirror 8 and a position sensor (PSD) 21 as one of the area sensors. The position sensor 21 and the virtual image point P in the eye E are conjugated with respect to the objective lens 2 and the lens 3, and the virtual images are formed on the light receiving surface 21a of the position sensor 21. The position sensor 21 is adapted to output an electric current corresponding to an imaged point position R on the light receiving surface 21a, i.e., a signal carrying X-, Y-information in the X-, Y-planes (see FIG. 3) as the light receiving surface 21a from four output terminals 22a through 22d. An analog calculating circuit 72, as will be described, calculates the imaged point position R on the light receiving surface 21a from an electric current value of the signal output from the four output terminals 22a through 22d.

The fixation mark projecting system 30 comprises an objective lens 2, a half mirror 7, a turret plate 31, a collimator lens 11, a mirror 12, a half mirror 32, fixation mark 33, and a lamp 34. The fixation mark 33 and the eye fundus Er are generally conjugated with respect to the collimator lens 11. The turret plate 31 is formed with a plurality of windows not shown. Each of the windows is provided with a lens having a different focal length. Due to the foregoing arrangement, a patient can gaze at the fixation mark in well focus by selectively rotating the turret plate 31 even when the patient is suffered from hyperopia or myopia. Due to the foregoing, the eye E can be made in a foggy sight state even when the eye E is hyperopia or myopia.

Figure 2:
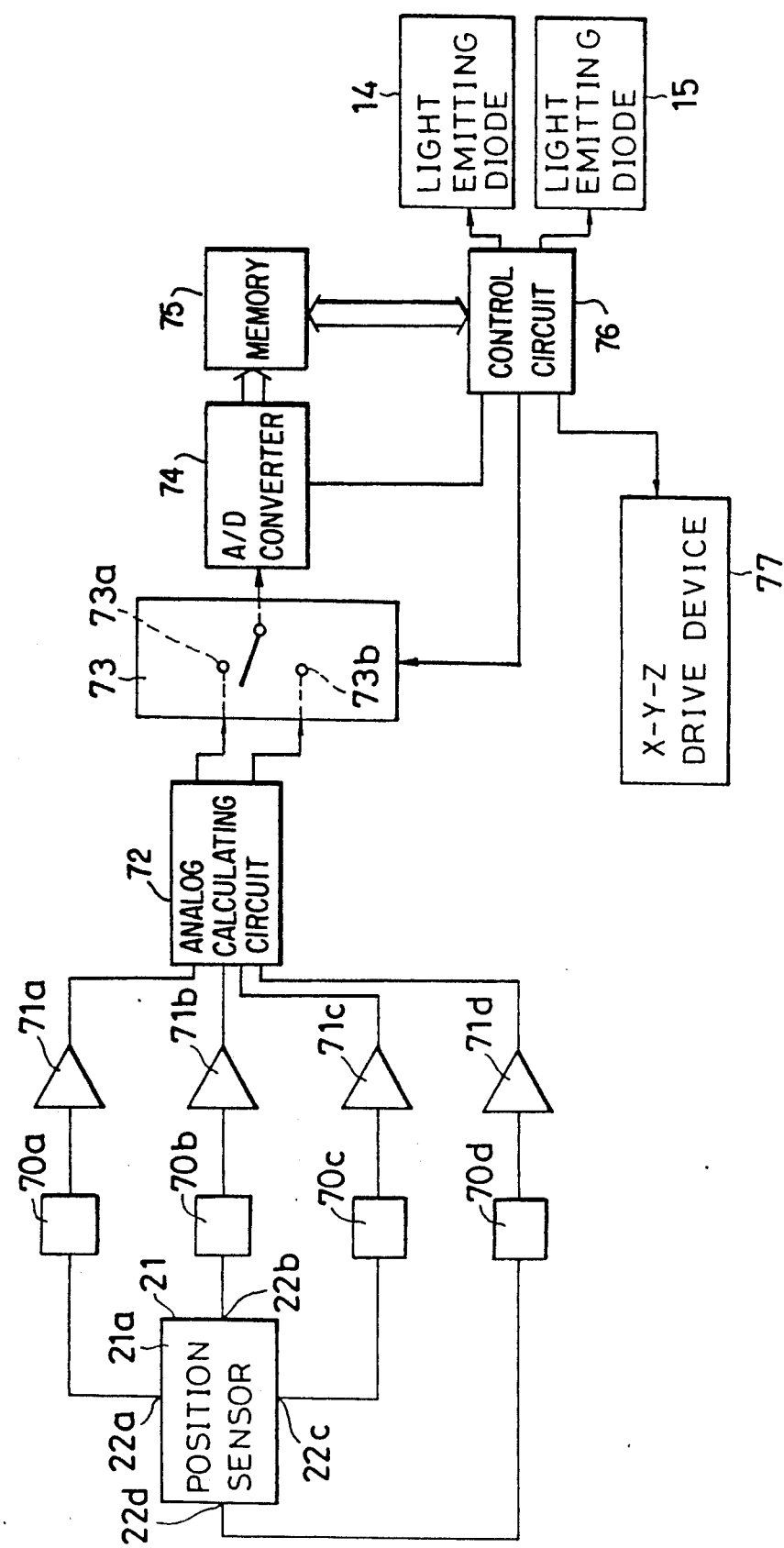
FIG. 2 is a block diagram showing a control system of the alignment apparatus of the noncontact type tonometer.

FIG. 2 is a block diagram showing a control system of the alignment apparatus of the noncontact type tonometer. In FIG. 2, 70a through 70d denote I/V converting circuit adapted to convert an electric current output from each of the output terminals 22a through 22d of the position sensor 21 to electric voltages corresponding to the values thereof, 71a through 71d denote amplifiers, and 72 denotes an analog calculating circuit adapted to calculate the (X,Y) coordinate position of the imaged point R on the light receiving surface 21a of the position sensor 21 shown in FIG. 3 according to the electric voltage output from each of the amplifiers 71a through 71d.

73 denotes an analog switch circuit which is adapted to close a contact 73a when the analog calculating circuit 72 is calculating the X-coordinate and close a contact 73b when the analog calculating circuit 72 is calculating the Y-coordinate. Therefore, the analog switch circuit 73, when the contact 73a is closed, outputs an electric voltage corresponding to the value of the X-coordinate obtained by the analog calculating circuit 72 through calculation and, when the contact 73b is closed, outputs an electric voltage corresponding to the Y-coordinate obtained by the analog calculating circuit 72 through calculation.

74 denotes an A/D converter adapted to convert an electric voltage of the X-, Y-coordinates output from the analog switch circuit 73 to a digital signal, and 75 denotes a memory circuit adapted to store therein the X-, Y-coordinates of a digital signal output from the A/D converter 74.

76 denotes a control circuit adapted to control the blinking of the light emitting diodes 14, 15, the switching action of the analog switch circuit 73, the converting timing of the A/D converter 74, and the like. This control circuit 76 determines whether the R point of the X-, Y-coordinates stored in the memory 75 is within the preset range S on the light receiving surface 21a as shown in FIG. 4. The control circuit 76, when the R point is within the preset range S, outputs an alignment completion signal and, when outside the preset range S, outputs a drive control signal for moving the apparatus body (not shown) in the alignment completing direction.

An X-Y-Z drive device 77 is provided with, for example, three motors and is adapted to move the apparatus body in the directions of the X-, Y-, Z-axes. In other words, the apparatus body is moved in the directions of the X-, Y-, Z-axes according to the drive control signal to align the axial line 60a of the nozzle 60 with the alignment axial line Ei of the eye E and make a predetermined distance between the eye and the nozzle 60. By the way, the I/V converting circuits 70a through 70d, the analog calculating circuit 72, the A/D converter 74, the memory circuit 75 and the control circuit 76 constitute the control circuit.

With the above-mentioned constitution, the function of the alignment apparatus of the noncontact type tonometer will now be described.

Presuming that the light emitting diode 14 is not lightening and the light emitting diode 15 is lightening, a target image due to the light emitting diode 14 is formed, as a virtual image P, in the eye E by the target projecting system 10. And, an image due to the virtual image is formed at $R_1$ point of the light receiving surface 21a of the position sensor 21 by the light receiving optical system 20 as shown in FIG. 3. Then, an electric current corresponding to the $R_1$ is output from the output terminals 22a through 22d of the position sensor 21, the coordinates $X_1$, $Y_1$ of the $R_1$ are calculated by the analog calculating circuit 72 from these electric current values, and the coordinates $X_1$, $Y_1$ of the $R_1$ point is stored in the memory circuit 75 through the analog switch 73 and the A/D converter 74. After the storage, the light emitting diode 15 is caused to be lightened and the light emitting diode 14 is caused to be extinguished by the control circuit 76, and a target image of the light emitting diode 15 is formed, as a virtual image P, on the eye E in the same manner as described. And, an image due to the virtual image P is formed at the $R_2$ point of the light receiving surface 21a of the position sensor 21 by the light receiving optical system 20. Then, an electric current corresponding to the $R_2$ point is output from the the output terminals 22a through 22d of the position sensor 21, the coordinates $X_2$, $Y_2$ of the $R_2$ point are calculated by the analog calculating circuit 72 from these electric current values, and the coordinates $X_2$, $Y_2$ of the $R_2$ point are stored in the memory circuit 75.

And, the control circuit 76 determines whether the imaging points $R_1$, $R_2$ stored in the memory circuit 75 are within the preset range S.

Presuming that the axial line 60a of the nozzle 60 and the alignment axial line Ei of the eye E are aligned with each other and the distance between the eye E and the nozzle 60 is a predetermined value, the imaging points $R_1$, $R_2$ are overlapped with each other at the center of the preset range S as shown in FIG. (a). In the foregoing state, the control circuit 76 outputs an alignment completion signal. Also, in the case as shown in FIG. 4(b), since the axial line 60a of the nozzle 60 and the alignment axial line Ei of the eye E are generally aligned with each other and the distance between the eye E and the nozzle 60 is a generally predetermined value, the control circuit 76 outputs an alignment completion signal. In this way, since the control circuit 76 determines whether the imaging points $R_1$, $R_2$ are within the preset range S and outputs an alignment completion signal, alignment of the noncontact type tonometer with respect to the eye E can be detected without fail irrespective of the reflectance of the eye E, affection of the disturbance light, etc.

And, when the alignment completion signal has been output, fluid is discharged from the nozzle 60 by a fluid generating device not shown. By this, the cornea Ea is made into applanation, and the applanation of the cornea Ea is detected by the detecting light projecting system 40 and the applanation detecting light receiving optical system 50. And, the eye pressure of the eye E is measured according to the fluid pressure when the applanation of the cornea Ea is detected.

In the case as shown in FIG. 4(c), the axial line 60a of the nozzle 60 and the alignment axial line Ei of the eye E are generally aligned with each other and the distance between the eye E and the nozzle 60 is shorter than the predetermined distance. In the foregoing state, the control circuit 76 outputs a drive control signal for moving the optical system backward. In the case as shown in FIG. 4(d), the axial line 60a of the nozzle 60 and the alignment axial line Ei of the eye E are generally aligned with each other and the distance between the eye E and the nozzle 60 is longer than the predetermined distance. In the foregoing state, the control circuit 76 outputs a drive control signal for moving the optical system forward.

In the case as shown in FIG. 4(e), the distance between the eye E and the nozzle 60 is generally the predetermined value and the axial line 60a of the nozzle 60 and the alignment is displaced in the vertical direction from the alignment axial line Ei of the eye E. In the foregoing state, the control circuit 76 outputs a drive control signal for moving the optical system in the vertical direction. In the case as shown in FIG. 4(f), the distance between the eye E and the nozzle 60 is generally the predetermined value and the axial line 60a of the nozzle 60 is displaced in the horizontal direction from the alignment axial line Ei of the eye E. In the foregoing state, the control circuit 76 outputs a drive control signal for moving the optical system in the horizontal direction.

And, upon receipt of the drive control signals, the X-Y-Z drive device 77 moves the apparatus body in the alignment completing direction. Therefore, the alignment is performed automatically.

In the above-mentioned embodiment, although, the positions of the imaging points $R_1$, $R_2$ of the targets are detected using the position sensor 21, the positions of the imaging points $R_1$, $R_2$ may be detected using, for example, a CCD as an area image sensor. In this case, if the targets are formed in shapes which can be distinguished from each other, the light emitting diodes 14, 15 are not required to be blinked alternately.

What is claimed is:

1. An alignment apparatus of a noncontact type tonometer, comprising:
    a target projecting system for forming first and second target images on an eye, said target projecting system including
    a half mirror,
        first and second light emitting sources for emitting light which impinges on said eye and respectively form said first and second target images, and
        said first and second light emitting sources being oriented such that light emitted from both said first and second light emitting sources is reflected by said half mirror before impinging on said eye;
    a fluid discharging nozzle for discharging a fluid along an axial line, the light emitted from both said first and second light emitting sources being directed along the axial line;
    a light receiving sensor for providing a position signal representative of the position of light projected thereon;
    an alignment light receiving optical system operatively coupled for receiving the first and second target images along the axial line of the nozzle and forming respective images of the first and second target images on said light receiving sensor; and
    a control unit operatively coupled to receive said position signal and responsively determine the positions of the respective images of the first and second target images formed on said light receiving sensor, said control unit outputting an alignment completion signal when such determined positions are within a preset range on said light receiving sensor.

2. An alignment apparatus of a noncontact type tonometer, comprising:
    a target projecting system for forming first and second target images on an eye, said target projecting system including
    a half mirror,
        first and second light emitting sources for emitting light which impinges on said eye and respectively form said first and second target images, and
        said first and second light emitting sources being oriented such that light emitted from both said first and second light emitting sources is reflected by said half mirror before impinging on said eye;
    a fluid discharging nozzle for discharging a fluid along an axial line, the light emitted from both said first and second light emitting sources being directed along the axial line;
    a light receiving sensor for providing a position signal representative of the position of light projected thereon;
    an alignment light receiving optical system operatively coupled for receiving the first and second target images along the axial line of the nozzle and forming respective images of the first and second target images on said light receiving sensor; and a calculating circuit for calculating positions of the first and second target images formed on said light receiving sensor;

a memory for storing therein the positions calculated by said calculating circuit; and a control circuit operatively coupled to receive the positions calculated by said calculating circuit and responsively output an alignment completion signal when the calculated positions are within a preset range on said light receiving sensor.

3. An alignment apparatus of a noncontact type tonometer according to claim 1 or claim 2, wherein said first and second light emitting sources are lighted alternately and said area sensor including a position sensor.

4. An alignment apparatus of a noncontact type tonometer according to claim 1 or claim 2, wherein said area sensor comprises a CCD.

5. An alignment apparatus of a noncontact type tonometer according to claim 2, wherein said first and second light emitting sources are lighted alternately and said area sensor including a position sensor.

6. An alignment apparatus of a noncontact type tonometer according to claim 2, wherein said area sensor comprises a CCD.

7. An alignment apparatus of a noncontact type tonometer, comprising:

a target projecting system for forming first and second target images on an eye, said target projecting system including
a half mirror,
first and second light emitting sources for emitting light which impinges on said eye and respectively form said first and second target images, and
said first and second light emitting sources being oriented such that light emitted from both said first and second light emitting sources is reflected by said half mirror before impinging on said eye;

a fluid discharging nozzle for discharging a fluid along an axial line, the light emitted from both said first and second light emitting sources being directed along the axial line;

a light receiving sensor for providing a position signal representative of the position of light projected thereon;

an alignment light receiving optical system operatively coupled for receiving the first and second target images along the axial line of the nozzle and forming respective images of the first and second target images on said light receiving sensor;

an apparatus body for containing said noncontact type tonometer;

a calculating circuit for calculating positions of the first and second target images formed on said light receiving sensor;

a memory for storing therein the positions calculated by said calculating circuit;

a control unit operatively coupled to receive the positions calculated by said calculating circuit and responsively output an alignment completion signal when the calculated positions stored in said memory are within a preset range on said light receiving position sensor, and to output a drive control signal for moving said apparatus body in an alignment completing direction when the calculated positions are outside the preset range; and a moving device for moving said apparatus body in the alignment completing direction according to the drive control signal.

* * * * *